(12) United States Patent
Deck

(10) Patent No.: US 10,939,858 B2
(45) Date of Patent: Mar. 9, 2021

(54) MEDICAL DEVICE AND METHOD FOR PRODUCING A MEDICAL DEVICE

(71) Applicant: ROCHE DIABETES CARE, INC., Indianapolis, IN (US)

(72) Inventor: Frank Deck, Niederkirchen (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 481 days.

(21) Appl. No.: 15/423,245

(22) Filed: Feb. 2, 2017

(65) Prior Publication Data

US 2017/0143243 A1 May 25, 2017

Related U.S. Application Data

(63) Continuation of application No. PCT/EP2015/067921, filed on Aug. 4, 2015.

(30) Foreign Application Priority Data

Aug. 6, 2014 (EP) .................................... 14180045

(51) Int. Cl.
*A61B 5/1486* (2006.01)
*A61B 5/145* (2006.01)
(Continued)

(52) U.S. Cl.
CPC ...... *A61B 5/14865* (2013.01); *A61B 5/14532* (2013.01); *A61B 5/14546* (2013.01);
(Continued)

(58) Field of Classification Search
None
See application file for complete search history.

(56) References Cited

U.S. PATENT DOCUMENTS

| 5,390,671 A | 2/1995 | Lord et al. |
| 6,360,888 B1 | 3/2002 | McIvor et al. |

(Continued)

FOREIGN PATENT DOCUMENTS

| CN | 102065908 A | 5/2011 |
| EP | 1 972 267 A1 | 9/2008 |

(Continued)

OTHER PUBLICATIONS

English translation of the International Preliminary Report on Patentability and Written Opinion of the International Searching Authority, PCT/EP2015/067921, dated Feb. 7, 2017.

(Continued)

*Primary Examiner* — Matthew Kremer
*Assistant Examiner* — Samuel C Kim
(74) *Attorney, Agent, or Firm* — Bose McKinney & Evans LLP

(57) ABSTRACT

An inventive medical device includes an implantable device, such as an electrochemical sensor. The implantable device has an implantable portion configured for insertion into a patient, a contact portion configured for connection to another device, and an interconnecting portion connecting the implantable portion and the contact portion. A housing is provided that has a first part that is removably connectable with a second part to form a sterile packaging to seal the implantable portion against a surrounding environment. The first part comprises a first sealing surface and the second part comprises a second sealing surface and the first and second sealing surfaces interact to form a sealing area. The interconnecting portion of the implantable device extends through the sealing area. An inventive method of producing the medical device is also disclosed.

18 Claims, 4 Drawing Sheets

(51) Int. Cl.
*A61B 50/30* (2016.01)
*A61B 5/00* (2006.01)
*A61L 2/08* (2006.01)
*A61L 2/20* (2006.01)

(52) U.S. Cl.
CPC ............ *A61B 5/6849* (2013.01); *A61B 50/30* (2016.02); *A61L 2/081* (2013.01); *A61L 2/087* (2013.01); *A61L 2/206* (2013.01); *A61B 2562/18* (2013.01); *A61B 2562/242* (2013.01); *A61L 2202/21* (2013.01)

(56) References Cited

U.S. PATENT DOCUMENTS

| | | | |
|---|---|---|---|
| 8,252,229 B2 | 8/2012 | Thomas et al. | |
| 2003/0050547 A1 | 3/2003 | Lebel et al. | |
| 2003/0149207 A1* | 8/2003 | Walter | C09J 179/06 |
| | | | 526/259 |
| 2003/0199893 A1* | 10/2003 | Boecker | A61B 5/1411 |
| | | | 606/181 |
| 2005/0083527 A1 | 4/2005 | Flaherty et al. | |
| 2007/0073129 A1 | 3/2007 | Shah et al. | |
| 2007/0197889 A1* | 8/2007 | Brister | A61B 5/1411 |
| | | | 600/347 |
| 2008/0234561 A1 | 9/2008 | Roesicke et al. | |
| 2008/0242962 A1 | 10/2008 | Roesicke et al. | |
| 2008/0255440 A1 | 10/2008 | Eilersen et al. | |
| 2009/0048499 A1* | 2/2009 | Glejbol | A61B 5/14532 |
| | | | 600/309 |
| 2009/0257911 A1 | 10/2009 | Thomas et al. | |
| 2010/0198034 A1 | 8/2010 | Thomas et al. | |
| 2011/0213225 A1 | 9/2011 | Bernstein et al. | |
| 2012/0184835 A1 | 7/2012 | Kube et al. | |
| 2013/0079675 A1* | 3/2013 | Stein | A61B 5/686 |
| | | | 600/587 |
| 2013/0137950 A1 | 5/2013 | Harttig et al. | |
| 2013/0150691 A1* | 6/2013 | Pace | A61B 5/14532 |
| | | | 600/347 |
| 2013/0184542 A1 | 7/2013 | Stafford | |
| 2013/0197333 A1 | 8/2013 | Petisce | |

FOREIGN PATENT DOCUMENTS

| | | |
|---|---|---|
| EP | 2 599 505 A1 | 6/2013 |
| JP | 2003-72861 A | 3/2003 |
| WO | WO 2009/126942 A2 | 10/2009 |
| WO | WO 2010/091005 A1 | 8/2010 |
| WO | WO 2010/091028 A1 | 8/2010 |
| WO | WO 2011/025549 A1 | 3/2011 |
| WO | WO 2012/118872 A2 | 9/2012 |

OTHER PUBLICATIONS

International Standard, ISO 14644-1:1999(E), Cleanrooms and associated controlled environments, Part 1: Classification of air cleanliness, First edition, May 1, 1999, pp. 1-24.
International Standard, ISO 14644-8:2006(E), Cleanrooms and associated controlled environments, Part 8: Classification of airborne molecular contamination, First edition, Aug. 15, 2006, pp. 1-26.

* cited by examiner

MEDICAL DEVICE AND METHOD FOR PRODUCING A MEDICAL DEVICE

RELATED APPLICATIONS

This application is a continuation PCT/EP2015/067921, filed Aug. 4, 2015, which claims priority to EP 14 180 045.8, filed Aug. 6, 2014, both of which are hereby incorporated herein by reference in their entireties.

BACKGROUND

The present invention relates to a medical device, an insertion kit and a method for producing a medical device. The method and the devices according to this disclosure may be used, e.g., for detecting at least one analyte in one or both of a body tissue or a body fluid. Devices in accordance with this disclosure may be applied in the field of diabetes care, both in home monitoring and in hospital applications. Additionally or alternatively, other uses are feasible.

In the art, a large number of devices and methods for producing devices for detecting at least one analyte in one or both of a body tissue or a body fluid are known. In general, such devices comprise portions, which are fully or at least partially implantable into a body tissue and which are suitable to detect and/or monitor bodily functions, preferably to detect and/or monitor one or more analytes. Without restricting the scope of this disclosure, in the following, mainly reference is made to the determination of glucose as an exemplary analyte.

In principle, a detection of at least one analyte in one or both of a body tissue or a body fluid can be performed discontinuously, wherein the analyte is detected within a sample of the bodily fluid of a user, and/or continuously, transcutaneously via continuous monitoring, preferably continuous monitoring of an analyte in the interstitium. Both methods may use, e.g., electrochemical sensors. In general, electrochemical sensors may comprise an electronic device adapted to generate an analyte-depending, electrical signal, which is detected and displayed, for example by one or more user interfaces.

In in-vivo measurements, devices are used, which comprise electrochemical sensors implantable into a body tissue. An active sensor portion of the electrochemical sensor, e.g., a sensor portion comprising electrodes of the electrochemical sensor, is implanted subcutaneously and converts the analyte, for example by using an enzyme, for example glucose oxidase, into a signal, in particular an electrical current. However, electronics, such as an evaluation unit and/or a control unit, of the device may be situated outside the body of the user. The detection, in particular the amplification of the signal of the electrical current is a major challenge, because in general amplification electronics of electrochemical sensors known in the art are highly sensitive to leakage currents such that a measurement result is influenced even by very small leakage currents. To prevent leakage currents, a connection, in particular via a connector, between the electrochemical sensor and the electronics of the device has to be designed liquid-tight. Further, connectors take up an unwanted large space. Thus, current devices are designed without using connectors often, such that the electrochemical sensor is mounted directly to a circuit board on which the electronics is situated.

For example, in U.S. Publication No. 2010/0198034 methods and devices to monitor an analyte in body fluid are described. In one embodiment, a data processing unit is coupleable to a sensor so that both devices are positioned in or on the user's body, with at least a portion of the analyte sensor positioned transcutaneously. The data processing unit may include a portion of the sensor which is encapsulated within or on a printed circuit board of the data processing unit with, for example, potting or other protective material. In addition, U.S. Publication No. 2011/0213225 discloses methods and devices to monitor an analyte in body fluid. Embodiments include in vivo analyte sensors and on body electronics that together provide body wearable sensor electronic assemblies, wherein in vivo analyte sensors are fully integrated with on body electronics. Further, in U.S. Publication No. 2010/0198034 an apparatus for insertion of a medical device in the skin of a subject is described.

However, the described devices, in particular the electrochemical sensors, are designed for implanting into a body of the user. Thus, sterilization of these devices generally is required. In the art, a large number of sterilization methods for sterilizing the described devices are known. Known methods of sterilization are radiation sterilization, in particular by electron and/or gamma radiation, methods and chemical sterilization methods, such as gas sterilization, in particular with ethylene oxide (EtO).

U.S. Pat. No. 8,252,229 discloses an assembly of an analyte sensor with an analyte sensor insertion device, including packaging the assembled analyte sensor and sensor insertion device in a substantially airtight seal and irradiating the packaged assembled sensor and sensor insertion device at a predetermined dose using one or more electron beam accelerators.

In U.S. Publication No. 2008/0242962 an in-vivo system for measuring an analyte concentration in a human or an animal body with at least one implantable sensor is described. In one embodiment, the sensor is arranged within a first housing chamber, which is sealed afterwards. Further, the housing chamber is irradiated by intensive radiation, for example electron radiation, such that the sensor and the insertion needle are sterilized.

U.S. Publication No. 2008/0234561 discloses a measurement system comprising an exchangeable sensor for in-vivo placement. In one embodiment, the sensor is arranged in a first housing chamber whereupon the chamber is sealed. Subsequently, the sensor in the housing chamber will be sterilized by irradiation. It is further described that especially appropriate are electron rays with a dose of at least 20 kGy. In particular, especially appropriate is an electron ray dose of 28 kGy.

However, sterilizing the device, in particular an assembly of the electrochemical sensor and electronics, by radiation may damage the electronics. On the other hand, sterilization methods usually used for sterilizing electronics, e.g., with EtO sterilization, may damage the electrochemical sensor, in particular the enzymes of the electrochemical sensor. Thus, sterilization methods are desirable, which allow for sterilizing both the electrochemical sensor and the electronics without damages. In the art, several attempts have been made to overcome this problem.

In U.S. Publication No. 2008/0255440 A1 a sensor package is described comprising an implantable sensor having an electrode area and an electric contact area. The electrode area is enclosed in a shielding packaging that is impermeable to micro-organism, in such a manner that the electric contact area extends outside the shielding packaging; and that the part of the sensor which is situated outside the shielding packaging is sterilized. The sensor can be sterilized by means of radiation, while the electronics can be sterilized separately by means of some other and less expensive sterilization procedure. Similar devices with electrical contacts outside a packaging or shielding packaging are described in JP 2003072861 or U.S. Publication No. 2003/0050547, too.

U.S. Publication No. 2013/0137950 discloses a method for sterilizing an implantable sensor for detecting at least one analyte in a body tissue. The implantable sensor is introduced within a packaging, which seals the sensor from bacteria and which houses a protective screen against radiation. The protective screen protects the electronic device against sterilization radiation and is arranged such that the sensor is sterilized by the sterilization radiation.

Despite these developments, there is a strong need for methods and devices allowing simultaneous sterilization of electrochemical sensors and electronics with different, suitable sterilization methods. Thus, electronic devices for readout of sensor signals of implantable sensors typically contain sensitive microelectronic devices such as semiconductor chips which typically suffer severe damage when exposed to energetic radiation such as electron beams. Contrarily, electrochemical sensors having a test chemical and/or electrodes capable of sensing the presence and/or concentration of an analyte typically are damaged by chemical sterilization such as sterilization by EtO. Thus, sensor electronics and electrochemical sensors typically might have to be sterilized independently, by appropriate sterilization means. However, after separately sterilizing these components, an assembly in a sterile environment will have to be performed. Assembly steps performed in a sterile environment, however, are generally limited with regard to their complexity and nature. Thus, as far as possible, soldering or bonding steps generally should not be performed in a cleanroom or sterile environment, due to the detrimental fumes or particles generated during these process steps. Further, performing process steps in a sterile environment typically significantly raises the costs of these process steps.

SUMMARY

This disclosure provides methods and devices for detecting at least one analyte in one or both of a body tissue or a body fluid which address the above-mentioned shortcomings and challenges of known methods and devices. Specifically, methods and devices are disclosed which are capable of providing a medical device with sterilized portions to be implanted within the body of the user and/or is in contact with the body of the user.

As used in the following, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B," "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, as used in the following, the terms "preferably," "more preferably," "particularly," "more particularly," "specifically," "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

Further, it should be understood that various structural terms used throughout this disclosure and claims should not receive a singular interpretation unless it is made explicit herein. By way of non-limiting example, the terms "contact portion," "sealing surface," and "sensor," to name just a few, should be interpreted when appearing in this disclosure and claims to mean one or more or at least one. All other terms used herein should be similarly interpreted unless it is made explicit that a singular interpretation is intended.

In a first aspect of this disclosure, a medical device is disclosed, comprising at least one implantable device having at least one implantable portion adapted for at least partially being implanted into a body tissue of a user. The implantable device further has at least one contact portion connected to the implantable portion. Further, the medical device comprises at least one housing. The housing is configured to receive the implantable portion. The housing is configured to provide a sterile packaging such that the implantable portion is sealed against a surrounding environment. The housing comprises at least one first part and at least one second part. The first part and the second part are removable connectable to form the sterile packaging. The first part comprises at least one first sealing surface and the second part comprises at least one second sealing surface. The first and second sealing surfaces interact to form a sealing area. The implantable device has an interconnecting portion connecting the implantable portion and the contact portion. The interconnecting portion is led through the sealing area.

As used herein, the term "medical device" generally refers to an arbitrary device configured to one or more of detecting, determining, and monitoring an analyte and/or a concentration of an analyte in the body tissue of the user. The medical device may be used in the field of home care as well as in the field of professional care, such as in hospitals.

As further used herein, the term "analyte" may refer to an arbitrary element, component or compound which may be present in a body fluid and the concentration of which may be of interest for a user. Preferably, the analyte may be or may comprise an arbitrary chemical substance or chemical compound which may take part in the metabolism of the user, such as at least one metabolite. As an example, the at least one analyte may be selected from the group consisting of glucose, cholesterol, triglycerides, lactate. Additionally or alternatively, however, other types of analytes may be used and/or any combination of analytes may be determined. Generally, an arbitrary type of body fluid may be used. Preferably, the body fluid is a body fluid which is present in a body tissue of the user, such as in the interstitial tissue. Thus, as an example, the body fluid may be selected from the group consisting of blood and interstitial fluid. However, additionally or alternatively, one or more other types of body fluids may be used. The body fluid generally may be contained in a body tissue.

The term "implantable device" generally refers to an arbitrary element comprising at least one implantable portion. As will be outlined in further detail below, the implantable device can be a medical instrument such as an implantable sensor for detecting at least one analyte in the body tissue; a cannula; a tube. As further used herein, the term "implantable portion" generally refers to an arbitrary element which is adapted to at least partly be implanted into the body tissue of the user. As further used herein, the term "at least partly implantable into a body tissue of the user" refers to the fact that the implantable portion is adapted to have appropriate dimensions to be inserted into the body tissue of the user, such as into subcutaneous tissue, and, further, that the implantable portion is biocompatible in order to remain in the body tissue for an elongated time period, such as for several days or even several weeks or several months. Further, as used herein, the phrase "implantable into a body tissue" is used synonymously with "at least partially implantable into a body tissue." Thus, as an example, the implantable portion or at least the implantable part of the implantable portion may have a biocompatible coating, such as at least one semipermeable membrane, which prevents the sensor material from migrating into the body tissue and, still, which is permeable to the at least one analyte. Further, the implantable portion may have an elongated shape, as will be outlined in further detail below, such as an elongated shape having a length of 5 mm to 50 mm. Other dimensions are possible. The implantable portion, as an example, may have a total volume of less than 3 $cm^2$, such as of less than 2 $cm^2$ or even of less than 1 $cm^2$.

The term "implant" refers to the fact that the implantable portion may be inserted fully or partially into the body tissue. Thus, in the following, the terms "implant" and "insert" will be used as synonyms. Generally, during implantation and/or during use of the implantable portion, the implantable portion may fully or partially penetrate the skin of the user. Thus, the implantable portion preferably may be embodied as a transcutaneous implantable portion.

As generally used within this disclosure, the term "user" may refer to a human being or an animal, independent from the fact that the human being or animal, respectively, may be in a healthy condition or may suffer from one or more diseases. As an example, the user may be a human being or an animal suffering from diabetes. However, additionally or alternatively, the teachings of this disclosure may be applied to other types of users.

As used herein, the term "contact portion connected to the implantable portion" refers to an element adapted to interact with other elements of the medical device, in particular adapted to connect the implantable device to other elements of the medical device. The contact portion is connected to the implantable portion connection. The connection may be a permanent connection or a releasable and/or reversible connection. In one embodiment, the implantable portion and the contact portion may be designed as one element. As will be described in detail below, the contact portion may comprise one or more electrical contacts of the implantable portion.

In general, the housing is an arbitrary element which provides protection to the implantable portion against environmental influences, in particular one or more of: mechanical influences from the outside; chemical influences, e.g., against moisture and/or gas; influences from micro-organisms such as germs, bacteria, viruses. The housing may provide a full enclosure against the surrounding environment. The housing may be at least partially made of a rigid material. In particular, the housing may be designed as a rigid housing, i.e., a housing which is not visibly deformed by forces usually occurring during a use of the implantable portion. A rigid material may be understood as a material which is not visibly and/or macroscopically deformed by forces usually occurring at usual loads, for example loads less than 1, 2, 3 or 5 N. However, embodiments wherein the housing can be at least partially made as a deformable housing, i.e., a housing which may be at least partially deformed by forces usually occurring during a use of the implantable portion, without losing its protection effect are feasible.

The housing is configured to receive the implantable portion. Generally, the term "configured to receive," as used herein, refers to that the housing is configured to surround the implantable portion. In particular, the implantable portion may be inserted in the housing and/or may be permanently and/or reversibly mounted within the housing.

A "sterile packaging" may be understood as a packaging that seals the implantable portion against the surrounding environment, such as against ingression of microorganisms. The term "surrounding environment," as used herein, refers to arbitrary environmental influences, in particular one or both of: chemical influences, e.g., moisture and/or gas; influences from micro-organisms such as germs, bacteria, viruses. As further used herein, the term "to seal" refers to close off the surrounding environment, in particular in micro-organism tight fashion. In a preferred embodiment, the housing may be made at least partially of a gas-tight material, preferably an EtO impermeable material.

As used herein, the term "at least one first part and at least one second part of the housing" generally refers to two arbitrary portions of the housing. As noted above, it shall be understood that the terms "first part" and "second part," and any other structural aspect of this disclosure for that matter, means "at least one," whether or not the term "at least one" is used. The housing may be configured as a two-component housing. For example, the housing may comprise two equal and/or different large halves. However, embodiments in which the housing may comprise three or more components are feasible. The first part and the second part are removable connectable to form the sterile packaging. As used herein, the terms "removable connectable" and "removably connectable" are used interchangeably and refer to a non-permanent connection of the first and second part, i.e., the parts can be connected and then disconnected. Similarly, "removably connecting" refers to connecting the parts such that they can later be disconnected, if desired. The first and second parts may be removably connectable by one or both of: a form-fit connection; a force-fit connection. In a preferred embodiment, the first and second parts may be connectable by a snap-fit connection.

The first part comprises at least one first sealing surface and the second part comprises at least one second sealing surface. As used herein, the term "sealing surface" of the first and second part in general refers to arbitrary portions of the first and second part adapted to connect and configured to seal the first and the second part in a connected state. In general, the sealing surfaces may be formed arbitrarily. For example, the sealing surfaces may be designed such that the first sealing surface and the second sealing surface fit to each other, so that one of the first sealing surface and the second sealing surface may be configured to one or more of sliding, moving or being inserted into the other one of the first sealing surface and the second sealing. In one embodiment, the first and the second sealing surfaces may be ring-shaped sealing surfaces. In one embodiment, one or both of the first part and the second part comprise at least one sealing lip.

As mentioned above, the first and second sealing surfaces interact to form a sealing area. As used herein, the term "sealing area" refers to an area which is formed by the first and the second sealing surfaces in a connected state of the first and the second part of the housing. As used herein, the term "interact to form a sealing area" refers to that one of the first sealing surface and the second sealing surface connects the other one of the first sealing surface and the second sealing surface, e.g., by pressing, resting etc.

In one embodiment, one or both of the first and second part, in the sealing area, at least partially may be made of a deformable material, preferably an elastic material. The deformable material may be selected from the group consisting of: an elastomeric material; a thermoplastic material, such as polypropylene; a thermoplastic elastomer.

As described above, the implantable device has an interconnecting portion connecting the implantable portion and the contact portion. The interconnecting portion may be understood to mean an arbitrary element adapted to connect the implantable portion and the contact portion. In an embodiment, the interconnecting portion may be designed integral, in particular in one-piece, with the implantable portion and the contact portion. For example, the interconnecting portion may be arranged between the implantable portion and the contact portion.

As used herein, the term "is led through the sealing area" refers to a protrusion of the interconnecting portion through the sealing area, i.e., the interconnecting portion extends through the sealing area. In a preferred embodiment, the interconnecting portion may be clamped between the first and the second sealing surfaces. The interconnecting portion may be pressed onto one of the first or second sealing surface by the other one of the first and second sealing surface.

The implantable device may comprise at least one of: an implantable sensor for detecting at least one analyte in the body tissue; a cannula; a tube. For example, the cannula may be a needle having a central lumen for receiving the implantable sensor during insertion. Preferably, the cannula is a slotted cannula. As further used herein, the term "implantable sensor" refers to an arbitrary element which is adapted for detecting, quantitatively and/or qualitatively, at least one analyte in the body tissue. The implantable sensor preferably comprises at least one sensor material, wherein the sensor material is adapted to perform at least one detectable reaction in the presence of the analyte. The sensor material preferably may be a sensor material selected from the group consisting of: an optical sensor material, wherein the optical sensor material is adapted to perform at least one optically detectable detection reaction in the presence of the analyte; an electrochemical sensor material, wherein the electrochemical sensor material is adapted to perform at least one electrically detectable detection reaction in the presence of the analyte, such as an electrically detectable redox reaction.

The implantable sensor preferably may comprise at least one flexible substrate, such as a flexible substrate having an elongated shape, wherein the flexible substrate may extend into the body tissue of the user. The flexible substrate, as an example, may fully or partially be made of one or more of a paper material, a cardboard material, a plastic material, a metallic material, a ceramic material or any combination thereof such as a laminate of two or more of the named materials. As an example, the flexible substrate may contain one or more plastic foils. The flexible substrate may have a thickness of less than 3 mm, such as of less than 1 mm, such as a thickness measured perpendicular to a plane of extension of the flexible substrate. Specifically in case the implantable sensor is an electrochemical sensor, the implantable sensor may have two or more electrodes applied to the substrate, such as at least one working electrode and at least one further electrode, such as at least one counter electrode and/or at least one reference electrode. For potential examples of the implantable sensors, reference may be made to the prior art documents listed above. Additionally or alternatively, other types of implantable sensors may be used.

In an embodiment, the housing may be at least partially cylindrical, such as cylindrical with a circular cross-section or cylindrical with a polygonal cross-section. The term "at least partially cylindrical" may be understood such, that in general the housing has a cylindrical shape. However, parts of the housing may be designed non-cylindrical. In this embodiment, the housing may have a longitudinal axis, wherein the implantable portion received within the sterile packaging at least partially extends parallel to the longitudinal axis, preferably along the longitudinal axis. The term "at least partially extends parallel" can be understood such that deviations from a parallel extension are possible. The implantable portion, as an example, may extend at an angle of less than 25°, such as at an angle of less than 10° or at an angle of less than 5° from the longitudinal axis. The contact portion may be at least partially bent away from the longitudinal axis. For example, the contact portion may be at least partially bent away from the longitudinal axis to allow a connection of the contact portion with other elements of the medical device. Additionally or alternatively, other embodiments in which the housing is non-cylindrical are feasible.

The contact portion may be adapted for providing at least one of a mechanical contact or an electrical contact to at least one further device interacting with the implantable device.

The contact portion may comprise at least one electrical contact. Thus, as an example, the electrical contact may comprise at least one electrical contact pad disposed on at least one carrier, such as on at least one substrate, e.g., a flexible substrate. The at least one contact pad, as an example, may have a rectangular or polygonal shape and, as an example, may comprise one or more metal layers adapted for being electrically connected via bonding, soldering or other electrically contacting means. The implantable device may be electrical connected with the contact portion via the electrical contact. The further device may comprise at least one electronic device, wherein the electronic device may be connected to the electrical contact outside the sterile packaging. As an example and as will be outlined in further detail below, the at least one electronic device may comprise at least one device for driving the implantable device and/or for reading out one or more signals generated by or provided by the implantable device.

The implantable device may comprise at least one electrochemical sensor for electrochemically detecting at least one analyte in one or both of a body tissue or a body fluid, wherein the at least one electronic device may comprise at least one electronic device for measuring and/or recording sensor signals generated by the electrochemical sensor. As used herein, the term "sensor signal" refers to arbitrary signals generated by the electrochemical sensor indicative of the presence of the analyte. The sensor signals may be generated at subsequent points in time, such as over a time period of several hours, several days, several weeks or even several months, such as over a time period of seven days. The sensor signal may be processed or pre-processed within a control device, such as by applying at least one evaluation or pre-evaluation algorithm to the sensor signal. Thus, the electronic device may comprise one or more of at least one data recording device, at least one date storage device, at least one data collection device and at least one control device.

The electrochemical sensor may be generated at least partially by screen printing. As used herein, the term "at least partially is generated" refers to the electrochemical sensor being generated completely by screen printing or that only parts of the electrochemical sensor may be generated by screen printing, wherein other parts of the electrochemical sensor may be generated by other production methods. The electronic device may be at least partially covered by at least one cover material. As used herein, the term "at least partially covered" refers to the electronic device being covered completely by the cover material or that only parts of the electronic device may be covered by the cover material. The electronic device at least partially may be covered at least partially by an elastomer, in particular a two-component silicone and/or a two-component polyurethane and/or a resin. The electronic device may be covered at least partially by an adhesive layer. For example, the electronic device may be over-molded by the adhesive layer after being covered by the cover material or vice versa. The adhesive layer may be configured to fix the electronic device on the body of the user. Additionally or alternatively, the medical device may comprise one or more mounting or fixing means for mounting or fixing the medical device or a part thereof, such as the at least one electronic device, to a body of the user. The at least one mounting or fixing means, as an example, may be or may comprise at least one adhesive tape, such as a plaster, and/or at least one strip or belt. Thus, as an example, a baseplate of the electronic device may be mounted to a skin of the user via at least one plaster and/or at least one strip or belt. Other mounting or fixing means are feasible and are known to the skilled person.

The implantable device may be made at least partially of a deformable material, such as of a flexible material. As used herein, the term "at least partially made of a deformable material" refers to that embodiments, wherein the implantable device may be made completely of a deformable material, and embodiments, wherein only parts of the implantable device may be made of a deformable material, are feasible. The implantable device may comprise at least one deformable substrate, such as a flexible substrate. For potential embodiments of the flexible substrate, reference may be made to the possibilities disclosed above.

The medical device further may comprise at least one transcutaneous insertion element. The transcutaneous insertion element may comprise at least one skin-penetrating element adapted to perforate the skin of the user. The transcutaneous insertion element may be adapted to guide the electrochemical sensor into the body tissue of the user. The transcutaneous insertion element may be selected from the group consisting of an insertion needle and an insertion cannula. The transcutaneous insertion element may be fixedly mounted to the first part of the housing. The transcutaneous insertion element may be connected to the first part of the housing by a molding process, such as an insert molding process, e.g., an injection insert molding process. In a connected state of the first part and the second part, the transcutaneous insertion element may be received within the sterile packaging and may be sealed against the surrounding environment by the housing.

The implantable portion, inside the sterile packaging, may be received at least partially within a lumen of the transcutaneous insertion element. The term "lumen" may be understood as a cavity, such as an elongated cavity, disposed within the transcutaneous insertion element. As an example, the transcutaneous insertion element may comprise at least one slot, such as a fully or partially opened slot, wherein the interior of the slot may form the lumen. The implantable portion may fully or partially be received within the slot. As used herein, the term "received at least partially within a lumen" refers to that at least parts of the implantable portion insertable into the body tissue of the user, in particular parts of the electrochemical sensor adapted to detect the analyte, more particular parts of the electrochemical sensor comprising electrodes of the electrochemical sensor, may be received within the lumen of the transcutaneous insertion element. However, at least the interconnecting portion of the implantable portion may be arranged outside the slot of the transcutaneous insertion element.

For example, the implantable device and/or the implantable portion may be pre-bent. Thus, the pre-bent implantable portion may be introduced into the slot in such a way that the parts of the implantable portion insertable into the body tissue of the user are arranged within the slot and the at least one contact portion is arranged outside the slot, such as extending at an angle from a longitudinal axis of the transcutaneous insertion element. As an example, the implantable device may be pre-bent such that the implantable portion and the contact portion form an angle of 5° to 120°, such as an angle of 10° to 90° or 20° to 70°, wherein the angle may be measured with respect to an outer surface of the housing parallel to the longitudinal axis of the transcutaneous insertion element and in direction to the further device, e.g., a body patch, interacting with the implantable portion. Other arrangements are feasible. The interconnecting portion may comprise a constriction, wherein the constriction allows for the implantable portion inside the lumen to be connected to the contact portion. Thus, an elongated opening of the slot may be narrower than a wider part inside the slot receiving the implantable portion, wherein the constricted interconnecting portion extends through the narrow slot to the outside of the slot.

The housing, such as the first part of the housing, further may comprise at least one mechanical interface, wherein the medical device is connectable to an insertion device by the mechanical interface. As used herein, the term "mechanical interface" generally refers to an arbitrary element or a combination of elements of the medical device which is adapted to interact with at least one mechanical interface of a second element in order to generate a mechanical connection between the medical device and the other element, in particular the insertion device. The insertion device may be adapted for mechanically inserting the implantable part into a body tissue of the user.

The mechanical interface may comprise at least one of: a groove, a constriction; a hook; a shoulder; a protrusion; an opening. Other types of mechanical interfaces may be used additionally or alternatively. The insertion device may comprise at least one driving mechanism for driving the skin-penetration element of the transcutaneous insertion element into the body tissue. The driving mechanism, as an example, may comprise at least one actuator adapted for forcefully moving the skin-penetration element through the skin into the body tissue. Thus, as an example, the driving mechanism may comprise at least one spring-based driving mechanism, adapted for transforming a mechanical energy stored in one or more springs into a movement of the skin-penetration element. Driving mechanisms of this fashion are generally known in the art, such as from U.S. Pat. No. 6,360,888. Thus, for specific details of the embodiment of the driving mechanism, reference may be made to this document. However, additionally or alternatively, other types of driving mechanisms may be used.

The insertion device may comprise at least one mechanical interface adapted to engage the mechanical interface of the medical device. Thus, the insertion device may comprise at least one insertion device mechanical interface. The mechanical interface of the insertion device may be adapted to reversibly engage the mechanical interface of the medical device, thereby generating a fixed spatial relationship between the medical device and the insertion device during insertion of the implantable portion into the body tissue. As used herein, the term "fixed spatial relationship" generally may refer to the fact that, in a connected state, the connected components, such as the mechanical interfaces of the medical device and the insertion device, form a connected unit comprising the two components in a predetermined orientation and/or distance. The mechanical interfaces may be adapted to form a form-fit or force-fit connection.

In a further aspect, an insertion kit, comprising at least one medical device according to the above described medical device, is disclosed. The insertion kit comprises further at least one insertion device. The insertion device is adapted for mechanically interfacing with the medical device into a body tissue of a user. As used herein, the "insertion kit" is an assembly of a plurality of components, wherein the components each may function and may be handled independently from each other, wherein the components of the insertion kit may interact to perform a common function. Thus, the insertion kit may comprise a plurality of components, wherein each component may be handled individually, independent from the other components, and may perform at least one function independently, wherein, further, all components or groups of components comprising at least two of the components may be combined, such as by physically connecting these components, in order to perform a common function implying functionality from the connected components. For a description of possible embodiments and definitions of the medical device and the insertion device, reference can be made to the above-mentioned medical device and insertion device according to this disclosure.

In a further aspect, a method for producing a medical device is disclosed. The method comprises the method steps disclosed in further detail below. The method steps, as an example, may be performed in the given order. However, a different order is also feasible. Further, one or more or even all of the method steps may be performed in parallel or in a timely overlapping fashion. Further, one or more or even all of the method steps may be performed once or repeatedly.

The method comprises providing at least one implantable device having at least one implantable portion adapted for at least partially being implanted into a body tissue of a user. The implantable device further has at least one contact portion connected to the implantable portion.

The method further comprises providing at least one housing. The housing is configured to receive the implantable portion. The housing provides a sterile packaging such that the implantable portion is sealed against a surrounding environment. The housing comprises at least one first part and at least one second part.

The method further comprises removably connecting, in particular (i.e., optionally) in a cleanroom or under cleanroom conditions or under other conditions, the first part and the second part to form the sterile packaging. The first part comprises at least one first sealing surface and the second part comprises at least one second sealing surface. The first and second sealing surfaces interact to form a sealing area. The implantable device has an interconnecting portion connecting the implantable portion and the contact portion.

The method comprises leading the interconnecting portion through the sealing area.

For a description of possible embodiments and definitions of devices used in the method, reference can be made to the above-mentioned devices according to this disclosure. Thus, the method may be adapted for producing a medical device according to one or more of the embodiments disclosed above or disclosed in further detail below. Still, other embodiments are feasible.

The removable connection of the first and second part may optionally be performed in a cleanroom or under cleanroom conditions. As used herein, the term "cleanroom" refers to an environment with a controlled level of environmental additives, as environmental pollution and/or contamination. In general, a cleanroom or cleanroom environment may be classified according to a number of particles per volume of air. Several cleanroom standards are available, such as ISO 14644-1 cleanroom standard, BS 5295 cleanroom standard or GMP EU classification. As an example, a cleanroom class ISO 8 respectively Grade D or better may be used. The cleanroom further may be a sterile room and/or may provide a sterile environment.

The interconnecting portion may be clamped in between the first and second sealing surfaces. In an embodiment, the interconnecting portion may be pressed onto one of the first or second sealing surface by the other one of the first and second sealing surface.

The first and second parts may be connected by one or both of: a form-fit connection; a force-fit connection. The first and the second part may be fit together in such a way that one of the first part and the second part may interlock in the other one of the first part and the second part. The first part may be removed from the second part in a removing direction along the longitudinal axis of the housing. Further, the connection of the first and the second part may be configured in such a way that a rotation and/or twist around the longitudinal axis is not possible. The first and second parts may be connected by a snap-fit connection. The second part of the housing may be removed from the housing before usage.

The method may comprise at least one radiation sterilization step, wherein in the radiation sterilization step the implantable portion may be exposed to sterilizing radiation within the housing. In general, a sterilization step may be an arbitrary process, wherein micro-organisms are killed and/or destroyed. In particular, micro-organisms may be killed and/or destroyed such that after sterilization process a multiplication of micro-organism is no longer possible. Here, the sterilization may be performed by irradiating the implantable portion with sterilizing radiation. In particular, the sterilizing radiation may be a particle radiation. The sterilizing radiation may comprise one or more of: electron radiation, preferably $\beta$-radiation; electromagnetic radiation, preferably $\gamma$-radiation. For example, the electron radiation may have an energy of 1.0 MeV to 10 MeV, preferably an energy of 2 MeV to 3 MeV and more preferably an energy of 2.5 MeV. As an example, the sterilizing radiation may provide a dose of at least 10 kGy, such as at least 20 kGy or at least 25 kGy.

The contact portion may be adapted for providing at least one of a mechanical contact or an electrical contact to at least one further device interacting with the implantable device. The contact portion may comprise at least one electrical contact. The further device may comprise at least one electronic device, wherein the electronic device may be connected to the electrical contact outside the sterile packaging. The implantable device may comprise at least one electrochemical sensor for electrochemically detecting at least one analyte in one or both of a body tissue or a body fluid, wherein the at least one electronic device may comprise at least one electronic device for measuring and/or recording sensor signals generated by the electrochemical sensor. The electrochemical sensor at least partially may be generated by screen printing.

The method may comprise at least partially covering the electronic device by at least one cover material. The method may comprise at least partially covering the electronic device by an elastomer, in particular two-component silicone and/or a two-component polyurethane and/or a resin. The method may comprise at least partially covering the electronic device by an adhesive layer. The covering processes may be performed in a non-cleanroom environment.

The method may comprise a testing step, wherein the implantable device may be tested, such as before receiving the implantable portion in the housing. As used here, a "testing step" may be an arbitrary process, wherein various properties of the implantable device may be tested. In particular, the electrochemical properties may be tested. In the testing step, the implantable device may be non-sterile. As used herein, the term "non-sterile" refers to a state of the implantable device before exposing the implantable device to a sterilization process, in particular a radiation sterilization step.

The configuration of the medical device may allow the method for producing a medical device according to this disclosure to be performed without sterilizing the electronic device. This waiver of sterilizing the electronic device may reduce production costs and provide logistical advantages. Alternatively, the electronic device may fully or partially be sterilized by chemical sterilization, such as by gas sterilization using at least one sterilizing gas, such as sterilization by using ethylene oxide. The chemical sterilization may take place after receiving the implantable portion in the housing and after sealing the implantable portion against the surrounding environment, such that the implantable portion remains unaffected by the chemical sterilization. The housing may be made at least partially of a gas-tight material, preferably an ethylene oxide impermeable material.

The method may comprise at least one attaching step, wherein the electronic device may be connected to the at least one electrical contact by one or more of welding, soldering or bonding. The attaching step may be performed in a non-cleanroom environment. As used herein, a "non-cleanroom environment" may be an arbitrary environment outside a cleanroom environment, in particular an environment filled with ambient air. In a preferred embodiment, the attaching step may be performed after a radiation sterilization step of the implantable device.

The medical device further may comprise at least one transcutaneous insertion element. The transcutaneous insertion element may be selected from the group consisting of an insertion needle and an insertion cannula. The transcutaneous insertion element may be fixedly mounted to the first part of the housing. The transcutaneous insertion element may be connected to the first part by a molding process. The transcutaneous insertion element may be connected to the first part by an insert molding process, e.g., an injection insert molding process. In a connected state of the first part and the second part, the transcutaneous insertion element may be received within the sterile packaging and is sealed against the surrounding environment by the housing. The implantable portion, inside the sterile packaging, may be received at least partially within a lumen of the transcutaneous insertion element. The transcutaneous insertion element may comprise at least one slot, wherein the implantable portion may be received within the slot. The interconnecting portion may comprise a constriction, wherein the constriction may allow for the implantable portion inside the lumen to be connected to the contact portion. The implantable portion may be pre-bent before the implantable portion is received within the slot. The receiving of the implantable portion within the lumen of the transcutaneous insertion element may be performed in a cleanroom.

The housing further may comprise at least one mechanical interface, wherein the medical device is connected to an insertion device by the mechanical interface. The insertion device may be an inserter. The connection of the medical device to an insertion device by the mechanical interface may be performed in a non-cleanroom environment.

In a preferred embodiment, the medical device may comprise the implantable portion, in particular the electrochemical sensor, which may be mounted fixedly together with the transcutaneous insertion element within the housing, preferably a first part of the housing. In a connected state of the first and the second part of the housing, the sealing area may ensure a protrusion of the interconnecting portion and may prevent ingress of micro-organisms, in particular during further production steps after mounting the first and second part of the method for producing the medical device, and during a storage period. Thus, elements that have to be kept sterile may be arranged within the housing. Outside the housing further elements may be arranged, such as the electronic device and the mechanical interface. The housing, in particular the sterile packing provided by the housing, allows separate sterilization of the electrochemical sensor, together with the transcutaneous insertion element, and the electronic device, and ensures sterility during further production steps after mounting the first and second part of the method for producing the medical device, and during the storage period. Thus, it may be possible to apply different sterilization methods suitable for the element to be sterilized and it may be possible to mount the implantable device and electronic device in a non-cleanroom environment. Further, the mechanical interface may ensure connecting the medical device and the further devices easily. The second part of the housing may be removed from the housing before usage.

Further, in a further preferred embodiment, the implantable portion may be arranged within the housing and may be sterilized by a radiation sterilization step. In this preferred embodiment, the electronic device may be connected to the implantable device and the electronic device, implantable device assembly may be exposed to sterilization gas, in particular to EtO. The housing may be made at least partially of a gas-tight material, in this case preferably of an ethylene oxide impermeable material. Thus, the housing may ensure preventing the implantable device to be exposed to EtO. Thus, it may be possible to produce a medical device with sterilized elements inside the housing and sterilized electronics outside the housing.

Summarizing the findings of this disclosure, the following embodiments are preferred:

Embodiment 1

A medical device, comprising at least one implantable device having at least one implantable portion adapted for at least partially being implanted into a body tissue of a user, the implantable device further having at least one contact portion connected to the implantable portion, the medical device further comprising at least one housing, wherein the housing is configured to receive the implantable portion, wherein the housing is configured to provide a sterile packaging such that the implantable portion is sealed against a surrounding environment, wherein the housing comprises at least one first part and at least one second part, wherein the first part and the second part are removable connectable to form the sterile packaging, wherein the first part comprises at least one first sealing surface and wherein the second part comprises at least one second sealing surface, wherein the first sealing surface and the second sealing surface interact to form a sealing area, wherein the implantable device has an interconnecting portion connecting the implantable portion and the contact portion, wherein the interconnecting portion is led through the sealing area.

Embodiment 2

The medical device according to the preceding embodiment, wherein the implantable device comprises at least one of: an implantable sensor for detecting at least one analyte in a body tissue; a cannula; a tube.

Embodiment 3

The medical device according to any one of the preceding embodiments, wherein the interconnecting portion is clamped in between the first sealing surface and the second sealing surface.

Embodiment 4

The medical device according to any one of the preceding embodiments, wherein the interconnecting portion is pressed onto one of the first sealing surface or second sealing surface by the other one of the first sealing surface and the second sealing surface.

Embodiment 5

The medical device according to any one of the preceding embodiments, wherein the first sealing surface and the second sealing surface are ring-shaped sealing surfaces.

Embodiment 6

The medical device according to any one of the preceding embodiments, wherein the housing at least partially is cylindrical.

Embodiment 7

The medical device according to the preceding embodiment, wherein the housing has a longitudinal axis, wherein the implantable portion received within the sterile packaging at least partially extends parallel to the longitudinal axis.

Embodiment 8

The medical device according to the preceding embodiment, wherein the contact portion at least partially is bent away from the longitudinal axis.

Embodiment 9

The medical device according to any one of the preceding embodiments, wherein the housing at least partially is made of a rigid material.

Embodiment 10

The medical device according to any one of the preceding embodiments, wherein one or both of the first part and the second part, in the sealing area, at least partially are made of a deformable material.

Embodiment 11

The medical device according to the preceding embodiment, wherein the deformable material is selected from the group consisting of: an elastomeric material; a thermoplastic material; a thermoplastic elastomer.

Embodiment 12

The medical device according to any one of the preceding embodiments, wherein the housing at least partially is made of a gas-tight material.

Embodiment 13

The medical device according to any one of the preceding embodiments, wherein the first part and the second part are connectable by one or both of: a form-fit connection; a force-fit connection.

Embodiment 14

The medical device according to any one of the preceding embodiments, wherein the first part and the second part are connectable by a snap-fit connection.

Embodiment 15

The medical device according to any one of the preceding embodiments, wherein one or both of the first part and the second part comprise at least one sealing lip.

Embodiment 16

The medical device according to any one of the preceding embodiments, wherein the contact portion is adapted for providing at least one of a mechanical contact or an electrical contact to at least one further device interacting with the implantable device.

Embodiment 17

The medical device according to the preceding embodiment, wherein the contact portion comprises at least one electrical contact.

Embodiment 18

The medical device according to the preceding embodiment, wherein the further device comprises at least one electronic device, wherein the electronic device is connected to the electrical contact outside the sterile packaging.

Embodiment 19

The medical device according to the preceding embodiment, wherein the implantable device comprises at least one electrochemical sensor for electrochemically detecting at least one analyte in one or both of a body tissue or a body fluid, wherein the at least one electronic device comprises at least one electronic device for measuring and/or recording sensor signals generated by the electrochemical sensor.

Embodiment 20

The medical device according to the preceding embodiment, wherein the electrochemical sensor at least partially is generated by screen printing.

Embodiment 21

The medical device according to any one of the three preceding embodiments, wherein the electronic device at least partially is covered by at least one cover material.

Embodiment 22

The medical device according to any one of the four preceding embodiments, wherein the electronic device at least partially is covered by an elastomer, in particular two-component silicone and/or a two-component polyurethane and/or a resin.

Embodiment 23

The medical device according to any one of the five preceding embodiments, wherein the electronic device at least partially is covered by an adhesive layer.

Embodiment 24

The medical device according to any one of the preceding embodiments, wherein the implantable device at least partially is made of a deformable material.

Embodiment 25

The medical device according to the preceding embodiment, wherein the implantable device comprises at least one deformable substrate.

Embodiment 26

The medical device according to any one of the preceding embodiments, wherein the medical device further comprises at least one transcutaneous insertion element.

Embodiment 27

The medical device according to the preceding embodiment, wherein the transcutaneous insertion element is selected from the group consisting of an insertion needle and an insertion cannula.

Embodiment 28

The medical device according to any one of the two preceding embodiments, wherein the transcutaneous insertion element is fixedly mounted to the first part of the housing.

Embodiment 29

The medical device according to the preceding embodiment, wherein the transcutaneous insertion element is connected to the first part by a molding process.

Embodiment 30

The medical device according to any one of the four preceding embodiments, wherein, in a connected state of the first part and the second part, the transcutaneous insertion element is received within the sterile packaging and is sealed against the surrounding environment by the housing.

Embodiment 31

The medical device according to any one of the five preceding embodiments, wherein the implantable portion, inside the sterile packaging, at least partially is received within a lumen of the transcutaneous insertion element.

Embodiment 32

The medical device according to the preceding embodiment, wherein the transcutaneous insertion element comprises at least one slot, wherein the implantable portion is received within the slot.

Embodiment 33

The medical device according to any one of the two preceding embodiments, wherein the interconnecting portion comprises a constriction, wherein the constriction allows for the implantable portion inside the lumen to be connected to the contact portion.

Embodiment 34

The medical device according to any one of the preceding embodiments, wherein the housing further comprises at least one mechanical interface, wherein the medical device is connectable to an insertion device by the mechanical interface.

Embodiment 35

The medical device according to the preceding embodiment, wherein the insertion device is an inserter.

Embodiment 36

The medical device according to any one of the two preceding embodiments, wherein the mechanical interface comprises at least one of: a groove; a constriction; a hook; a shoulder; a protrusion; an opening.

Embodiment 37

An insertion kit, comprising at least one medical device according to any one of the preceding embodiments, further comprising at least one insertion device, wherein the insertion device is adapted for mechanically interfacing with the medical device and for at least partially implanting the implantable portion of the medical device into a body tissue of a user.

Embodiment 38

A method for producing a medical device, the method comprising providing at least one implantable device having at least one implantable portion adapted for at least partially being implanted into a body tissue of a user, the implantable device further having at least one contact portion connected to the implantable portion, the method further comprising providing at least one housing, wherein the housing is configured to receive the implantable portion, the housing providing a sterile packaging such that the implantable portion is sealed against a surrounding environment, wherein the housing comprises at least one first part and at least one second part, the method further comprising removably connecting the first part and the second part to form the sterile packaging, wherein the first part comprises at least one first sealing surface and wherein the second part comprises at least one second sealing surface, wherein the first sealing surface and the second sealing surface interact to form a sealing area, wherein the implantable device has an interconnecting portion connecting the implantable portion and the contact portion, wherein the method comprises leading the interconnecting portion through the sealing area.

Embodiment 39

The method according to the preceding embodiment, wherein the removable connection of the first part and the second part is performed in a cleanroom or under cleanroom conditions.

Embodiment 40

The method according to any one of the preceding embodiments directed to a method, wherein the interconnecting portion is clamped in between the first sealing surface and the second sealing surface.

Embodiment 41

The method according to the preceding embodiment, wherein the interconnecting portion is pressed onto one of the first sealing surface or the second sealing surface by the other one of the first and second sealing surface.

Embodiment 42

The method according to any one of the preceding embodiments directed to a method, wherein the first part and the second part are connected by one or both of: a form-fit connection; a force-fit connection.

Embodiment 43

The method according to any one of the preceding embodiments directed to a method, wherein the first part and the second part are connected by a snap-fit connection.

Embodiment 44

The method according to any one of the preceding embodiments, the method comprising at least one radiation sterilization step, wherein in the radiation sterilization step the implantable portion is exposed to sterilizing radiation within the housing.

Embodiment 45

The method according to the preceding embodiment, wherein the sterilizing radiation comprises one or more of: electron radiation, preferably β-radiation; electromagnetic radiation, preferably γ-radiation.

Embodiment 46

The method according to any one of the preceding embodiments directed to a method, wherein the contact portion is adapted for providing at least one of a mechanical contact or an electrical contact to at least one further device interacting with the implantable device.

Embodiment 47

The method according to the preceding embodiment, wherein the contact portion comprises at least one electrical contact.

Embodiment 48

The method according to the preceding embodiment, wherein the further device comprises at least one electronic device, wherein the electronic device is connected to the electrical contact outside the sterile packaging.

Embodiment 49

The method according to the preceding embodiment, wherein the implantable device comprises at least one electrochemical sensor for electrochemically detecting at least one analyte in one or both of a body tissue or a body fluid, wherein the at least one electronic device comprises at least one electronic device for measuring and/or recording sensor signals generated by the electrochemical sensor.

Embodiment 50

The method according to the preceding embodiment, wherein the electrochemical sensor at least partially is generated by screen printing.

Embodiment 51

The method according to any one of the three preceding embodiments, the method comprising at least partially covering the electronic device by at least one cover material.

Embodiment 52

The method according to any one of the four preceding embodiments, the method comprising at least partially covering the electronic device by an elastomer, in particular two-component silicone and/or a two-component polyurethane and/or a resin.

Embodiment 53

The method according to any one of the five preceding embodiments, the method comprising at least partially covering the electronic device by an adhesive layer.

Embodiment 54

The method according to any one of the six preceding embodiments, wherein the method comprises a testing step, wherein the implantable device is tested, preferably before receiving the implantable portion in the housing.

Embodiment 55

The method according to the preceding embodiment, wherein in the testing step the implantable device is non-sterile.

Embodiment 56

The method according to any one of the eight preceding embodiments, wherein the electronic device is sterilized by chemical sterilization, preferably by gas sterilization using at least one sterilizing gas, more preferably sterilization by using ethylene oxide.

Embodiment 57

The method according to the preceding embodiment, wherein the chemical sterilization takes place after receiving the implantable portion in the housing and after sealing the implantable portion against the surrounding environment, such that the implantable portion remains unaffected by the chemical sterilization.

Embodiment 58

The method according to any one of the 10 preceding embodiments directed to a method, the method comprising at least one attaching step, wherein the electronic device is connected to the at least one electrical contact by one or more of welding, soldering or bonding.

Embodiment 59

The method according to any one of the 11 preceding embodiments, wherein the attaching step is performed in a non-cleanroom environment.

Embodiment 60

The method according to any one of the two preceding embodiments, wherein the attaching step is performed after a radiation sterilization step of the implantable device.

Embodiment 61

The method according to any one of the preceding embodiments directed to a method, wherein the medical device further comprises at least one transcutaneous insertion element.

Embodiment 62

The method according to the preceding embodiment, wherein the transcutaneous insertion element is selected from the group consisting of an insertion needle and an insertion cannula.

Embodiment 63

The method according to any one of the two preceding embodiments, wherein the transcutaneous insertion element is fixedly mounted to the first part of the housing.

Embodiment 64

The method according to the preceding embodiment, wherein the transcutaneous insertion element is connected to the first part by a molding process.

Embodiment 65

The method according to any one of the four preceding embodiments, wherein, in a connected state of the first part and the second part, the transcutaneous insertion element is received within the sterile packaging and is sealed against the surrounding environment by the housing.

Embodiment 66

The method according to any one of the five preceding embodiments, wherein the implantable portion, inside the sterile packaging, at least partially is received within a lumen of the transcutaneous insertion element.

Embodiment 67

The method according to the preceding embodiment, wherein the transcutaneous insertion element comprises at least one slot, wherein the implantable portion is received within the slot.

Embodiment 68

The method according to any one of the two preceding embodiments, wherein the interconnecting portion comprises a constriction, wherein the constriction allows for the implantable portion inside the lumen to be connected to the contact portion.

Embodiment 69

The method according to any one of the two preceding embodiments, wherein the implantable device and/or the implantable portion is pre-bent before the implantable portion is received within the slot.

Embodiment 70

The method according to any one of the four preceding embodiments, wherein the receiving of the implantable portion within the lumen of the transcutaneous insertion element is performed in a cleanroom.

Embodiment 71

The method according to any one of the preceding embodiments directed to a method, wherein the housing further comprises at least one mechanical interface, wherein the medical device is connected to an insertion device by the mechanical interface.

Embodiment 72

The method according to the preceding embodiment, wherein the insertion device is an inserter.

Embodiment 73

The method according to any one of the two preceding embodiments, wherein the connection of the medical device to an insertion device by the mechanical interface is performed in a non-cleanroom environment.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

Further optional features and embodiments will be disclosed in more detail in the subsequent description of preferred embodiments, preferably in conjunction with the dependent claims. Therein, the respective optional features may be realized in an isolated fashion as well as in any arbitrary feasible combination, as the skilled person will realize. The scope of the invention is not restricted by the disclosed embodiments. The embodiments are schematically depicted in the Figures. Therein, identical reference numbers in these Figures refer to identical or functionally comparable elements.

DESCRIPTION

The embodiments described below are not intended to be exhaustive or to limit the invention to the precise forms disclosed in the following description. Rather, the embodiments are chosen and described so that others skilled in the art may appreciate and understand the principles and practices of this disclosure.

Figure 1:
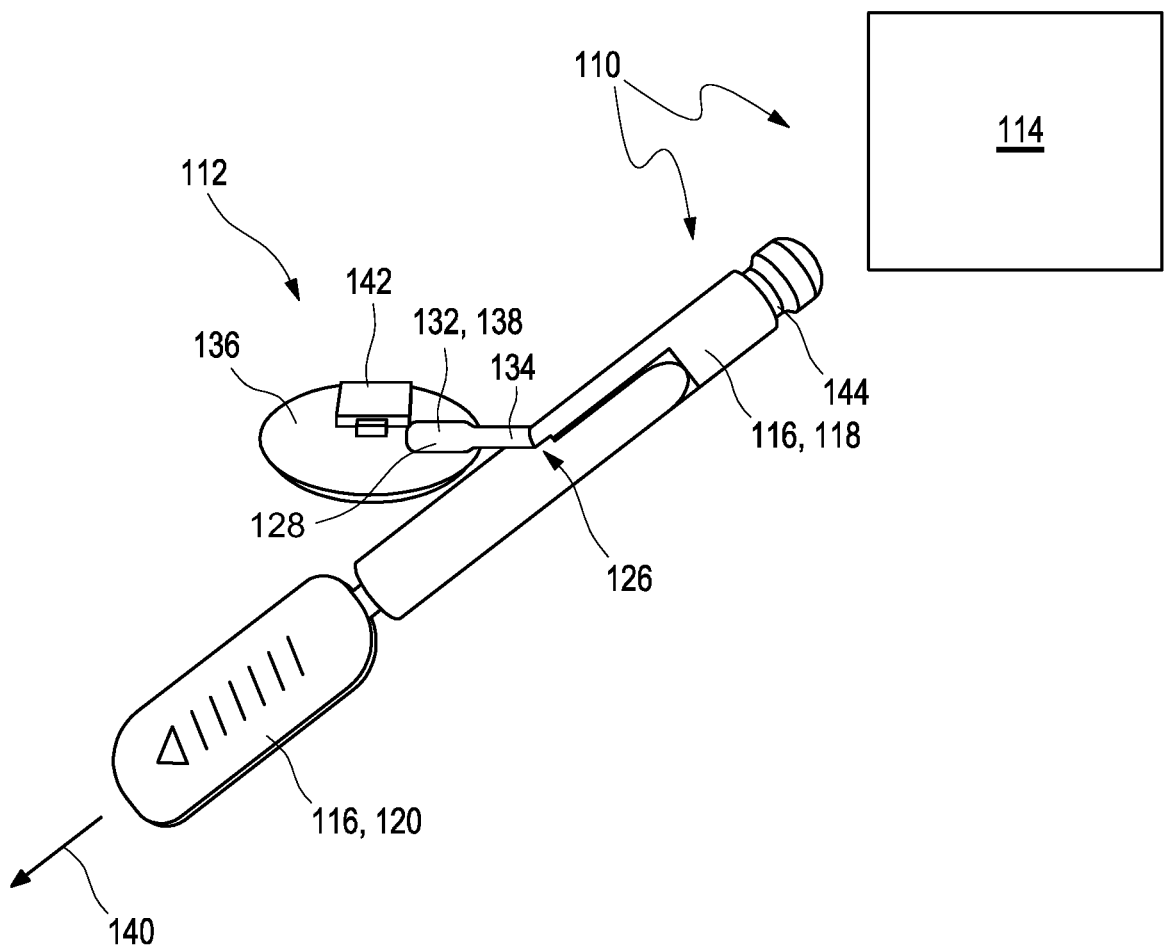
FIG. 1 shows an embodiment of an insertion kit comprising at least one medical device according to this disclosure.

In FIG. 1, an embodiment of an insertion kit 110 comprising at least one medical device 112 according to this disclosure is shown. The kit 110 comprises at least one insertion device 114, which is in FIG. 1 depicted symbolically only. The insertion device 114 may be a commercially available insertion tool or inserter used for sensors and infusion sets. The medical device 112 comprises at least one housing 116. The housing may be at least partially made of a rigid material. The housing 116 comprises at least one first part 118 and at least one second part 120. The first part 118 and the second part 120 are removable connectable to form a sterile packaging. In FIG. 1, an embodiment is shown, wherein the first part 118 and the second part 120 may be in a connected state. The first part 118 and the second part 120 may be connectable by one or both of: a form-fit connection; a force fit connection.

Figure 2:
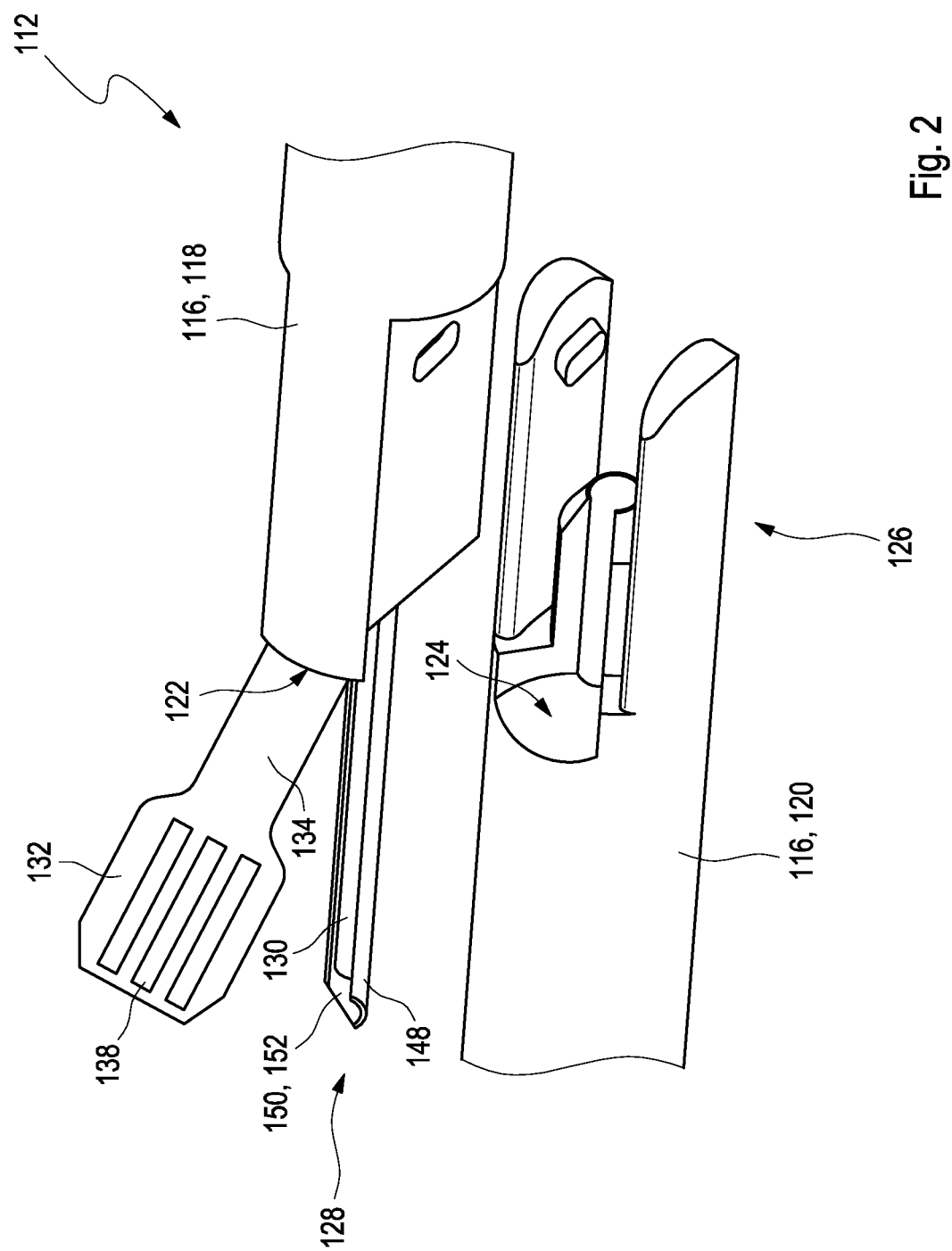
FIG. 2 shows an embodiment of removable connection of a first and a second part of the housing according to this disclosure.
Figure 3A:
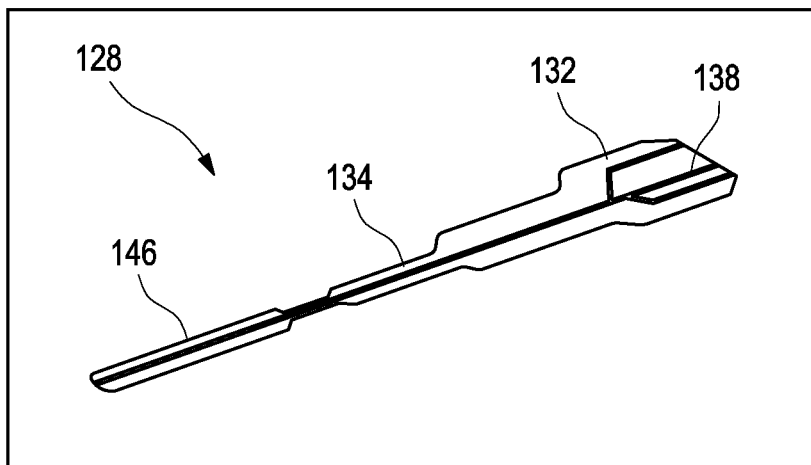
FIG. 3 shows an overview of a method for producing a medical device according to this disclosure.
Figure 3B:
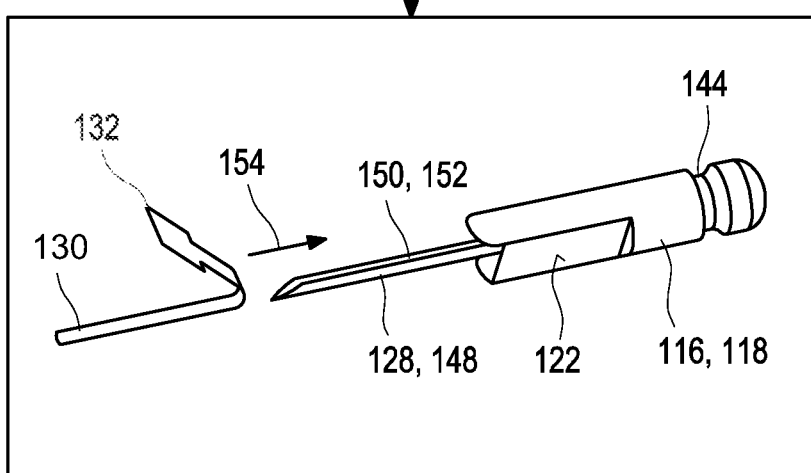
Figure 3C:
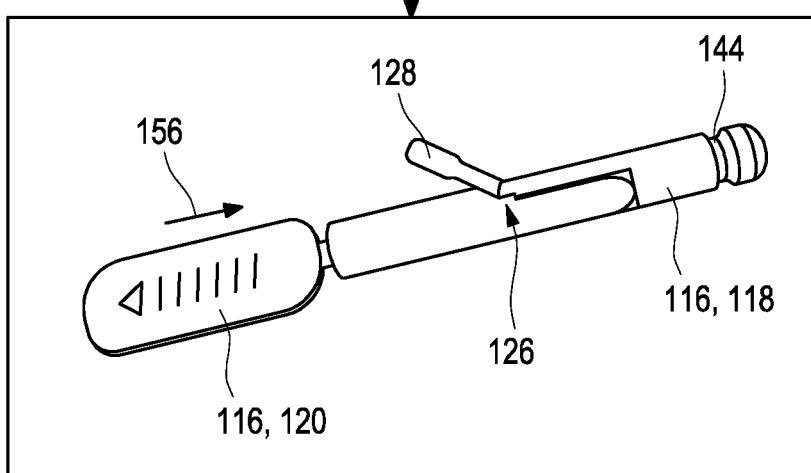
Figure 3D:
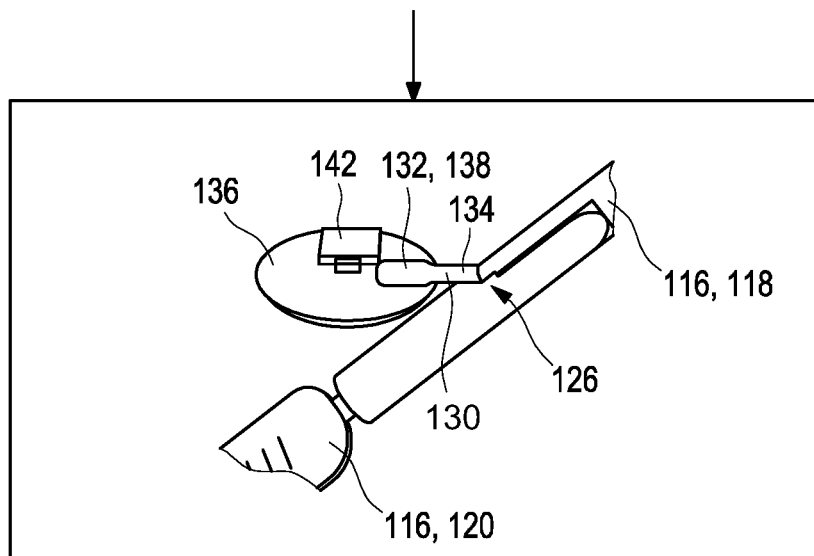
Figure 3E:
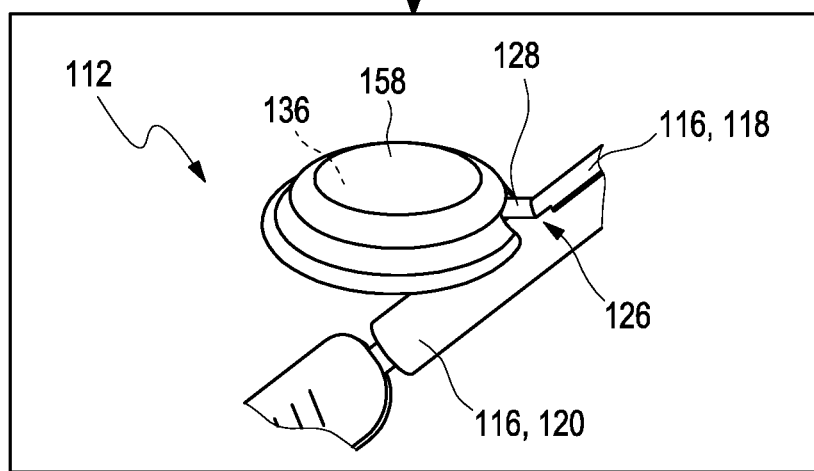
Figure 3F:
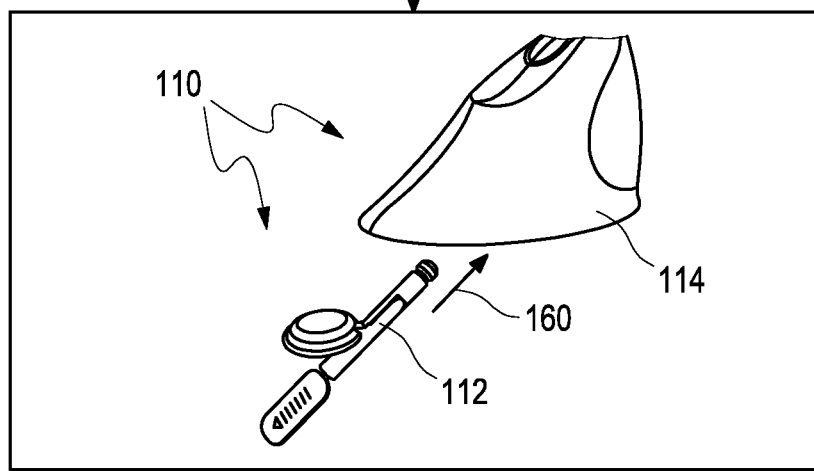

FIG. 2 shows an embodiment of removable connection of the first part 118 and a second part 120 of the housing 116 according to this disclosure. The first part 118 comprises at least one first sealing surface 122 and the second part 120 comprises at least one second sealing surface 124. The first sealing surface 122 and the second sealing surfaces may be ring-shaped sealing surfaces. The first sealing surface 122 and the second sealing surface 124 interact to form a sealing area 126. The medical device 112 comprises at least one implantable device 128 having at least one implantable portion 130 adapted for at least partially being implanted into a body tissue of a user. The implantable device 128 may comprise at least one of the following medical instruments: an implantable sensor for detecting at least one analyte in a body tissue; a cannula; a tube. The housing 116 is configured to receive the implantable portion 130. The housing 116 is configured to provide a sterile packaging such that the implantable portion 130 is sealed against a surrounding environment. In particular, the housings may ensure protecting the implantable portion 130 from influences from micro-organisms. The implantable device 128 further has at least one contact portion 132 connected to the implantable portion 130. The implantable device 128 has an interconnecting portion 134 connecting the implantable portion 130 and the contact portion 132. The contact portion 132 may be adapted for providing at least one of a mechanical contact or an electrical contact to at least one further device 136, e.g., sketched in FIG. 1, interacting with the implantable device 114. The contact portion may comprise at least one electrical contact 138.

The interconnecting portion 134 is led through the sealing area 126. The interconnecting portion 134 may be clamped in between the first sealing surface 122 and the second sealing surface 124. The interconnecting portion 130 is pressed onto one of the first sealing surface 122 and the second sealing surface 124 by the other one of the first and second sealing surface 122, 124. The housing 116 may be made at least partially of a rigid material. Preferably, one or both of the first part 118 and the second part 120, in the sealing area 126, at least partially may be made of a deformable material, preferably an elastic material. The deformable material may be selected from the group consisting of: an elastomeric material; a thermoplastic material, e.g., polypropylene; a thermoplastic elastomer. In a preferred embodiment, the first part 118 and the second part 120 may comprise a sealing lip.

In FIG. 2, an embodiment is depicted, wherein the first part 118 and the second part 120 may be connectable by a snap-fit connection. For example, the first part 118 and the second part 120 may be configured according to the lock and key principle. The first part 118 may be partially inserted in one or more of a cavity within the second part; an opening of the second part; a mounting element of the second part; a reception element of the second part. The second part 120 may comprise at least one of: a groove; a constriction; a hook; a shoulder; a protrusion; an opening, wherein the first part 118 may comprise a counterpart. Further, one of the first part 118 and the second part 120 may be configured such that a twisting or rotation motion of the first part 118 may be prevented.

The housing 116, shown in FIG. 1, may be at least partially cylindrical. The housing 116 may have a longitudinal axis 140, wherein the implantable portion 130 received within the sterile packaging at least partially may extend parallel to the longitudinal axis 140, preferably along the longitudinal axis 140. The contact portion 132 may be at least partially bent away from the longitudinal axis 140. The further device 136 may comprise at least one electronic device 142, wherein the electronic device 142 may be connected to the electrical contact 138 outside the sterile packaging.

The housing 116 may comprise at least one mechanical interface 144. The medical device 112 may be connectable to the insertion device 114 by the mechanical interface 144. The mechanical interface 144 may comprise at least one of: a groove; a constriction; a hook; a shoulder; a protrusion; an opening. In the embodiment shown in FIG. 1, the mechanical interface 144 may comprise a groove.

With regard to further embodiments of the insertion kit 110 and medical device 112 according to this disclosure, reference can be made to the following description (FIG. 3) of the overview of a method for producing the medical device 112 according to this disclosure.

FIG. 3 shows an overview of an exemplary method for producing the medical device 112. Firstly, the implantable device 128 may be provided, as shown in partial Figure A of FIG. 3. The implantable device 128 may comprise at least one electrochemical sensor 146 for electrochemically detecting one analyte in one or both of a body tissue or a body fluid. The electrochemical sensor may be at least partially generated by screen printing. The implantable device 128 may be made of a deformable material, preferably a flexible material. The implantable device 128 may comprise at least one deformable substrate, preferably a flexible substrate. The method, such as step A, may comprise a testing step, wherein the implantable device 128 may be tested. For example, the electrochemical properties of the electrochemical sensor 146 may be tested. In the testing step, the implantable device 128 may be non-sterile.

Further, the medical device 112 may comprise at least one transcutaneous insertion element 148, as shown in partial Figure B of FIG. 3. The transcutaneous insertion element 148 may be selected from the group consisting of an insertion needle and an insertion cannula. The transcutaneous insertion element 148 may be fixedly mounted to the first part 118 of the housing 116. For example, the transcutaneous insertion element 148 may be connected to the first part 118 by a molding process, e.g., an insert molding process, e.g., an injection insert molding process. The implantable portion 130, inside the sterile packaging, at least partially may be received within a lumen 150 of the transcutaneous insertion element 148. The transcutaneous insertion element 148 may comprise at least one slot 152, wherein the implantable portion 130 is received within the slot 152. The interconnecting portion 134 may comprise a constriction, wherein the constriction may allow for the implantable portion 134 inside the lumen 150 to be connected to the contact portion 132. The implantable portion 130 may be pre-bent before the implantable portion 130 may be received within the slot 152 and may be inserted to the slot 152. Reference number 154 indicates an insertion direction of the pre-bent implantable portion 130. The receiving of the implantable portion 130 within the lumen 150 of the transcutaneous insertion element 148 may be performed in a cleanroom.

Next, as shown in partial Figure C of FIG. 3, the first part 118 and the second part 120 may be removable connected. The removable connection of the first part 118 and the second part 120 may be performed in a cleanroom. The first and the second sealing surfaces 122, 124 interact to form the sealing area 126. The interconnecting portion 134 may be clamped in between the first and second sealing surfaces 122, 124. The first part 118 and second part 120 may be connected by one or both of: a form-fit connection; a force-fit connection. Reference number 156 indicates a connection direction of the first part 118 and the second part 120. In a connected state of the first part 118 and the second part 120, the transcutaneous insertion element 148 may be received within the sterile packaging and may be sealed against the surrounding environment by the housing 116. The housing provides a sterile packaging such that the implantable portion 130 is sealed against the surrounding environment. The method may comprise at least one radiation sterilization step, wherein in the radiation sterilization step the implantable portion 130 may be exposed to sterilizing radiation within the housing 116. The sterilizing radiation may comprise one or more of: electron radiation, preferably β-radiation; electromagnetic radiation, preferably γ-radiation.

Further, as shown in partial Figure D of FIG. 3, the method may comprise at least one attaching step, wherein the electronic device 142 may be connected to the at least one electronic contact 138 by one or more of welding, soldering or bonding. The further device 136 may be connected to the implantable device 128. The contact portion 132 may be adapted for providing at least one of a mechanical contact or an electrical contact to the further device 136 interacting with the implantable device 128. Thus, the contact portion 132 may comprise the at least one electrical contact 138. The further device 136 may comprise the at least one electronic device 142. The at least one electronic device 142 may comprise at least one electronic device for measuring and/or recording sensor signals generated by the electrochemical sensor 146. The electronic device 142 may be connected to the electrical contact 138 outside the sterile packaging. The attaching step may be performed in a non-cleanroom environment. The attaching step may be performed after a radiation sterilization step of the implantable device 128.

If an application requires the electronic device 142 to be sterile, the electronic device 142 may be sterilized by chemical sterilization, preferably by gas sterilization using at least one sterilizing gas, more preferably sterilization by using ethylene oxide. The chemical sterilization takes place after receiving the implantable portion 130 in the housing 116 and after sealing the implantable portion 130 against the surrounding environment, such that the implantable portion 130 remains unaffected by the chemical sterilization. The housing 116 may be made at least partially of a gas-tight material, preferably an ethylene oxide impermeable material.

Further, as shown in partial Figure E of FIG. 3, the method may comprise at least partially covering the electronic device 142 by at least one cover material 158. In a preferred embodiment, the method may comprise at least partially covering the electronic device 142 by an elastomer, in particular two-component silicone and/or a two-component polyurethane and/or a resin. Additionally, the method may comprise at least partially covering the electronic device 142 by an adhesive layer, which is not depicted in the figures. The covering processes may be performed in a non-cleanroom environment.

Further, as shown in partial Figure F of FIG. 3, the medical device 112 may be connected to the insertion device 114 by the mechanical interface 144. For example, the medical device 112 may be at least partially introduced into the insertion device 114 by means of the interface 144. Reference number 160 indicates an introducing direction. The connection of the medical device 112 to the insertion device 114 by the mechanical interface 144 may be performed in a non-cleanroom environment.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMBERS 110 insertion kit
112 medical device
114 insertion device
116 housing
118 first part
120 second part
122 first sealing surface
124 second sealing surface
126 sealing area
128 implantable device
130 implantable portion
132 contact portion
134 interconnecting portion
136 further device
138 electrical contact
140 longitudinal axis
142 electronic device
144 mechanical interface
146 electrochemical sensor
148 transcutaneous insertion element 150 lumen
152 slot
154 insertion direction
156 connection direction
158 cover material
160 introducing direction

What is claimed is:

1. A medical device, comprising:
an implantable device having (i) an implantable portion adapted for at least partially being implanted into a body tissue of a user, (ii) a contact portion configured for connection to a further component, and (iii) an interconnecting portion connecting the implantable portion and the contact portion; and
a housing configured to receive the implantable portion, the housing comprising a first part removably connectable with a second part to form a sterile packaging to seal the implantable portion against a surrounding environment, wherein the first and second parts are configured such that removing the first part from the second part exposes the implantable portion for insertion in the body tissue of the user, wherein the first part comprises a first sealing surface and the second part comprises a second sealing surface and the first and second sealing surfaces interact to form a sealing area, wherein the interconnecting portion extends through the sealing area and wherein the contact portion is folded away from a longitudinal axis of the housing.

2. The medical device according to claim 1, wherein the implantable device comprises at least one of: an implantable sensor for detecting at least one analyte in one or both of a body tissue or a body fluid; a cannula; a tube.

3. The medical device according to claim 1, wherein the interconnecting portion is clamped between the first sealing surface and second sealing surface.

4. The medical device according to claim 1, wherein the housing is at least partially cylindrical and wherein the implantable portion received within the sterile packaging at least partially extends parallel to the longitudinal axis.

5. The medical device according to claim 1, wherein the first part and second part are removably connectable by one or more of: a form-fit connection; a force-fit connection; a snap-fit connection.

6. The medical device according to claim 1, wherein the contact portion is adapted for providing at least one of a mechanical contact or an electrical contact to a further component associated with the implantable device, wherein the contact portion comprises at least one electrical contact.

7. The medical device according to claim 6, wherein the implantable device comprises an electrochemical sensor for electrochemically detecting at least one analyte in one or both of a body tissue or a body fluid.

8. The medical device according to claim 1, further comprising a transcutaneous insertion element fixedly mounted to the first part of the housing.

9. An insertion kit, comprising at least one medical device according to claim 1 and further comprising at least one insertion device, wherein the insertion device is adapted for mechanically interfacing with the medical device and for at least partially implanting at least one implantable portion of the medical device into the body tissue of a user.

10. A method for producing a medical device, comprising:
providing an implantable device having (i) an implantable portion adapted for at least partially being implanted into a body tissue of a user, (ii) a contact portion configured for connection to a further component, and (iii) an interconnecting portion connecting the implantable portion and the contact portion;
providing a first housing part having a first sealing surface and providing a second housing part having a second sealing surface;
removably connecting the first housing part to the second housing part to form a sterile packaging within which the implantable portion is disposed; and
folding the contact portion away from a longitudinal axis of the housing;
wherein the step of removably connecting the first housing part and second housing part creates a sealing area between the first and second seals, and the interconnecting portion is led through the sealing area, wherein the first and second parts are configured such that removing the first part from the second part exposes the implantable portion for insertion in the body tissue of the user.

11. The method according to claim 10, wherein the step of removably connecting is performed in a cleanroom or under cleanroom conditions.

12. The method according to claim 10, further comprising at least one radiation sterilization step, wherein in the radiation sterilization step the implantable portion is exposed to sterilizing radiation within the housing.

13. The method according to claim 10, further comprising:
connecting an electrical contact of the contact portion to an electronic device located outside the sterile packaging;
after receiving the implantable portion in the housing and after sealing the implantable portion against the surrounding environment, sterilizing the electronic device by chemical sterilization, whereby the implantable portion remains unaffected by the chemical sterilization.

14. The method according to claim 13, further comprising an attaching step in which the electronic device is connected to the electrical contact by one or more of welding, soldering or bonding, wherein the attaching step is performed in a non-cleanroom environment.

15. The method according to claim 14, wherein the attaching step is performed after a radiation sterilization step of the implantable device.

16. A medical device, comprising:
a substantially flat implantable sensor having two oppositely facing broad sides and two lateral edges, an implantable portion adapted for at least partially being implanted into a body tissue of a user, a contact portion configured for connection to a further component, and an interconnecting portion connecting the implantable portion and the contact portion; and
a housing configured to receive the implantable portion, the housing comprising a first part removably connectable with a second part to form a sterile packaging to seal the implantable portion against a surrounding environment and the first and second parts are configured such that removing the first part from the second part entirely removes the housing from a tip of the implantable portion and exposes the implantable portion for insertion in the body tissue of the user, wherein the first part comprises a first sealing surface and the second part comprises a second sealing surface and the first and second sealing surfaces interact to form a sealing area, wherein the interconnecting portion extends through the sealing area, further wherein the first sealing surface presses onto one of the two broad sides and the second sealing surface presses onto the other of the two broad sides, whereby the interconnecting portion is sandwiched between the first and second sealing surfaces.

17. A method for producing a medical device, comprising:
providing a substantially flat implantable sensor having two oppositely facing broad sides and two lateral edges, an implantable portion adapted for at least partially being implanted into a body tissue of a user, a contact portion configured for connection to a further component, and an interconnecting portion connecting the implantable portion and the contact portion;
providing a first housing part having a first sealing surface and providing a second housing part having a second sealing surface;
removably connecting the first housing part to the second housing part to form a sterile packaging within which the implantable portion is disposed, wherein the first and second parts are configured such that removing the first part from the second part entirely removes the housing from a tip of the implantable portion and exposes the implantable portion for insertion in the body tissue of the user;
wherein the step of removably connecting the first housing part and second housing part comprises pressing the first sealing surface onto one of the two broad sides and pressing the second sealing surface onto the other of the two broad sides to sandwich the interconnecting portion between the first and second sealing surfaces, whereby a sealing area is created between the first and second sealing surfaces, and the interconnecting portion is led through the sealing area.

18. A medical device, comprising:
a substantially flat implantable sensor having two oppositely facing broad sides and two lateral edges, an implantable portion adapted for at least partially being implanted into a body tissue of a user, a contact portion configured for connection to a further component, and an interconnecting portion connecting the implantable portion and the contact portion; and
a housing configured to receive the implantable portion, the housing comprising a first part removably connectable with a second part to form a sterile packaging to seal the implantable portion against a surrounding environment and the first and second parts are configured such that removing the first part from the second part along a longitudinal axis of the implantable sensor exposes the implantable portion for insertion in the body tissue of the user, wherein the first part comprises a first sealing surface and the second part comprises a second sealing surface and the first and second sealing surfaces interact to form a sealing area, wherein the interconnecting portion extends through the sealing area, further wherein the first sealing surface presses onto one of the two broad sides and the second sealing surface presses onto the other of the two broad sides, whereby the interconnecting portion is sandwiched between the first and second sealing surfaces.

* * * * *